United States Patent [19]

Chu

[11] Patent Number: 5,116,113
[45] Date of Patent: May 26, 1992

[54] LASER EYE PROTECTIVE DEVICES

[75] Inventor: Nori Y. C. Chu, Shrewsbury, Mass.

[73] Assignee: American Optical Corporation, Southbridge, Mass.

[21] Appl. No.: 579,942

[22] Filed: Sep. 10, 1990

[51] Int. Cl.$^5$ ............................ G02C 7/10; G02B 5/22
[52] U.S. Cl. ..................................... 351/163; 359/885
[58] Field of Search ....................... 351/163, 164, 165; 359/885

[56] References Cited

U.S. PATENT DOCUMENTS 3,959,171 5/1976 Woodcock ........................... 428/428

Primary Examiner—Scott J. Sugarman
Attorney, Agent, or Firm—Fishman, Dionne & Cantor

[57] ABSTRACT

Laser protection is provided by utilizing certain organic polymers with carboxylic or sulfonic acid groups which exchange their protons with cupric or ferrous metal ions to form cupric or ferrous ion-containing polymers. In addition, laser protection is also provided utilizing organic polymers with functional groups which are capable of forming complexes with cupric or ferrous metal ions. The optical absorption of the metal ions (e.g., the transition metal and rare earth ions) in these two types of metal ion-containing polymers are similar to those in absorbing glasses and will provide absorption in the near IR portion of the spectrum (i.e., greater than 680 nm). Thus, metal ion-containing polymers can be as useful for laser eye protection as known absorbing glasses, while providing high visual transmittance and light weight.

8 Claims, No Drawings

LASER EYE PROTECTIVE DEVICES

BACKGROUND OF THE INVENTION

This invention relates generally to laser protective devices. More particularly, this invention relates to a laser protective device comprised of an ion containing polymer which is particularly well suited for protection from near IR lasers.

Currently, there are several technologies available for providing protection against laser threats. Some of these technologies have been developed to a level which offers protection against certain laser wavelengths. The technology using passive absorbing materials for protection against ruby and Nd:YAG laser wavelengths is well developed and has been deployed for over two decades. The absorbing materials currently being used are absorbing colored glasses and organic dyes.

Absorbing colored glasses and absorbing organic dyes have their own set of advantages and disadvantages. The advantages for absorbing glasses are their high visual transmittance and good abrasion resistance, while the disadvantages are lower impact resistance and greater weight. Absorbing organic dyes are relatively low in cost and compatible with polycarbonate which offers excellent protection against ballistic impact. However, their visual transmittances are lower than absorbing glasses at comparable levels of laser eye protection (LEP).

In view of the continued threat from lasers, there is a need for improved laser protection (i.e., eyewear), particularly for specific wavelengths such as near IR.

SUMMARY OF THE INVENTION

In accordance with the present invention, laser protection is provided by utilizing certain organic polymers with carboxylic or sulfonic acid groups which exchange their protons with cupric or ferrous ions to form cupric or ferrous ion containing polymers. In addition, laser protection is also provided utilizing organic polymers with functional groups which are capable of forming complexes with metal ions. The optical absorption of the cupric or ferrous metal ions (e.g., the transition metal and rare earth ions) in these two types of ion-containing polymers are similar to those in the absorbing glasses and will provide absorption in the near IR portion of the spectrum (i.e, greater than 680 nm). Thus, metal ion-containing polymers can be as useful for LEP as absorbing glasses, while providing high visual transmittance and light weight.

Furthermore, cupric or ferrous ion containing polymers are organic polymeric materials and are therefore compatible with suitable optically clear host materials including polycarbonate, which is used for ballistic fragmentation protection. Thus, metal ion containing polymers can have the advantage of known absorbing glasses and known absorbing organic dyes. These polymers may also offer a means to provide LEP devices with high visual transmittance and high impact resistance at lower costs, particularly for visors and spectacles.

The above-discussed and other features and advantages of the present invention will be appreciated and understood by those skilled in the art from the following detailed description.

DESCRIPTION OF THE PREFERRED EMBODIMENT

Absorbing filters are the proven methodology for providing laser eye protection (LEP). Such filters can be made of glass or plastics. Both have been used extensively in non-military environments and are widely available from several commercial manufacturers. Plastic absorbing filters use various organic dyes or pigments which are proprietary to each individual manufacturer for absorbing laser radiations.

The technology for making colored glasses spans most of human history. It is a well established fact that the color of a glass is imparted by the transition metal ion or the rare earth ion present in the glass composition as an impurity or as a deliberately added component. The color of the glass depends strongly on the nature and valence state of the ion in the glass. For instance, ferrous ions give a green tint to a glass while ferric ions impart a brown color. One known commercial glass series (i.e., KG-3) uses ferrous ions to give a broad absorption centered at 1100 nm. Cupric ions in another commercial glass series (i.e., BG-39) display a broad band absorption with a maximum at 850 nm.

The chemistry of organic dyes and pigments is well understood. The choice of dyes or pigments for absorbing laser wavelengths below 700 nm is extremely large if the visual transmittance is not a concern. However, the number of organic compounds which absorb above 700 nm is limited to a few classes of organic dyes. As in the case of dyes absorbing in the visible spectrum, organic dyes absorbing above 700 have a detrimental effect on the visual transmittance. Cellulose acetate propionate has been used as a substrate for LEP. However, polycarbonate is now the material of choice since it provides added protection against ballistic fragments.

In accordance with the present invention, laser protective devices comprised of cupric or ferrous metal ion containing polymers in an optically clear host material are provided which have the combined attributes of the high visual transmittance of BG-39 type glass and the strength and light weight of plastics. The laser protective devices of the present invention are comprised of two types of metal ion containing polymers which provide laser protection in the near IR. These two polymer types consist of ionomer and complex forming polymers.

Ionomer Polymers

Ion containing polymers represent a broad class of organic and inorganic systems with inorganic ions attached to a polymer chain or participating in a network formation. The common inorganic glasses and polyelectrolytes which have high ion content are two well known ion containing systems. Ionomers belong to a third class of ion containing polymers which have a low ion content and a low polarity polymer backbone. Therefore, ionomers synthesized with the desired cupric or ferrous transition metal ion will have the same absorption characteristics of KG and BG glasses and therefore may be a preferred component of the metal ion containing polymers of this invention.

An example of a suitable ionomer is a lithium and zinc cation partially neutralized poly(ethylene co-methacrylic acid) sold by DuPont under the trade name Surlyn. These modified polyethylenes possess remarkable clarity and tensile properties superior to those of conventional polyethylene. Another example of a suitable ionomer for use in the present invention includes poly(-butadiene-co-acrylonitrile-co-acrylic acid) manufactured by B.F. Goodrich. This material can be neutralized with zinc oxide or other zinc salts and plasticized to break ionic association at elevated temperatures. More recently, new families of ionomers have emerged that possess a wide variety of properties and have been used in many diverse applications. A list of ionomers which are suitable for use in the present invention is given in Table 1.

TABLE 1

IONOMERS

| Polymer System | Trade Name | Manufacturer |
| --- | --- | --- |
| ethylene-methacrylic acid copolymer | Surlyn | DuPont |
| butadiene-acrylic acid copolymer | Hycar | Goodrich |
| perfluorosulfonate ionomers | Nafion | DuPont |
| perfluorocarboxylate ionomers | Flemion | Asahi Glass |
| telechelic polybutadiene | Hycar | Goodrich |
| sulfonated ethylene-propylene-diene terpolymer | Ionic Elastomer | Uniroyal |
| poly(methylmethacrylate co-methacrylic acid) | | |
| poly(methylmethacrylate co-methacrylic acid) | | |
| styrene-acrylic acid copolymer | | |
| sulfonated polystyrene | | |
| sulfonated polypentenamer | | |
| telechelic polyisobutylene sulfonated ionomers | | |
| alkyl methacrylate-sulfonate copolymers | | |
| styrene-based polyampholytes | | |
| acid-amine ionomers | | |

The functional groups of ionomers with which ions can be exchanged to form salts are carboxylic acid or sulfonic acid. Typical ionomer structures can be illustrated as follows:

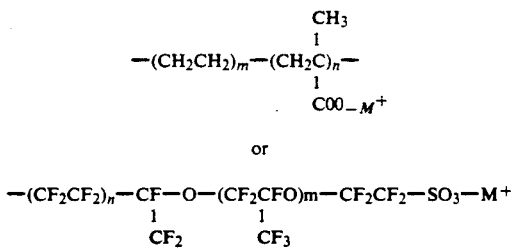

where $M^+$ is a cupric or ferrous metal ion.

The counterions used in commercial ionomers are usually sodium or zinc. Other alkali ions have also been used. In the scientific literature, many other metal ions, particularly the alkaline-earth and transition metal ions have been employed for salt formation.

Complex Forming Polymers

Another class of ion containing polymers suitable for the present invention contains functional groups which can form complexes with cupric or ferrous metal ions. This class of polymers differs from the ionomers in that the bonding between the metal ion and the polymer is not necessarily ionic. The ion contents of the polymers can be varied to a wider range than the ion containing polymers without significantly changing the polymer characteristics. Since the absorptivities of the transition metal ion and rare earth ions are relatively small compared to the organic dyes, high ion content of the polymer is desirable.

There are numerous complex forming ligands. They include ionic ions ($Cl^-$, $CN^-$ and $OH^-$), inorganic molecules $NH_3$, $CO$ and $CS_2$), organometallics ($SiR_3$), and organic molecules (2,2'-bipyridine, 1,2-diazene, and crown ether).

There are many classes of organic molecules which can form complexes with cupric or metal metal ions. Typical organic ligands are (1) nitrogen containing compounds such as 2,2'bipyridine, 1,10-phenanthroline, 1,2-diazene, phthalocyanines and porphyrins (2) oxygen containing compounds such as dibenzo-18-crown-6 ether and -diketone; and (3) sulfur containing compounds such as dithiocarbamates, and 1,2-dithiolene. Many of these ligands, particularly the nitrogen containing ones, have been incorporated into vinyl polymers as side chains.

In order to achieve high visual transmittance as in the absorbing glasses, the ligands should not have absorption in the visible. Therefore, only ligands which are not highly conjugated are suitable. Some typical examples are dibenzo-18-crown-6 ether, acetylacetonate and 2,2-bipyridine.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A laser eye protective device including:
   an optically clear organic polymeric host material; and
   at least one cupric or ferrous metal ion containing organic compound which absorbs light at a wavelength above about 680 nm, said metal ion containing compound being compatible with, and distributed in, said polymeric host material.

2. The device of claim 1, wherein said metal ion containing compound comprises:
   a salt of an organic ionomer having carboxylic or sulfonic acid functional groups and a cupric or ferrous ion.

3. The device of claim 1, wherein said metal ion containing organic compound comprises:
   a complex formed by a ligand and a cupric or ferrous ion.

4. The device of claim 3, wherein the ligand does not absorb visible light.

5. The device of claim 1, wherein the organic polymer host material is selected from the group consisting of cellulose acetate propionate and polycarbonate.

6. The device of claim 1, wherein the laser eye protective device exhibits a high visual transmittance and a high degree of laser protection which are substantially equal to the respective visual transmittance and degree of laser protection provided by an absorptive glass filter, and exhibits a substantially lower density and substantially increased impact resistance relative to a glass absorptive filter.

7. The device of claim 2, wherein the ionomer is selected from the group consisting of sulfonated polystyrene, sulfonated polypentenamer, telechelic polyisobutylene sulfonated ionomers, alkyl methacrylate-sulfonate copolymers, styrene-based polyampholytes and acid-amine ionomers.

8. The device of claim 3, wherein the ligand is selected from the groups consisting of dibenzo-18-crown-6-ether, acetylacetonate and 2,2-bipyridine.

* * * * *